（12） United States Patent
Nowatschin et al.

(10) Patent No.: US 11,045,276 B2
(45) Date of Patent: *Jun. 29, 2021

(54) MEDICAL HOLDING ARM HAVING ANNULAR LED DISPLAY MEANS

(71) Applicant: Brainlab Robotics GmbH, Munich (DE)

(72) Inventors: Stephan Nowatschin, Munich (DE); Maximilian Krinninger, Wessling-Oberpfaffenhofen (DE); Dominikus Gierlach, Munich (DE)

(73) Assignee: Brainlab Robotics GmbH, Munich (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/423,454

(22) Filed: May 28, 2019

(65) Prior Publication Data

US 2019/0274780 A1  Sep. 12, 2019

Related U.S. Application Data

(63) Continuation of application No. 15/751,846, filed as application No. PCT/EP2016/069167 on Aug. 11, 2016, now Pat. No. 10,342,636.

(30) Foreign Application Priority Data

Aug. 12, 2015  (EP) .................................... 15180826

(51) Int. Cl.
*F16M 13/00* (2006.01)
*A61B 90/50* (2016.01)
(Continued)

(52) U.S. Cl.
CPC .............. *A61B 90/50* (2016.02); *A61B 17/02* (2013.01); *A61B 34/30* (2016.02); *B25J 1/02* (2013.01);
(Continued)

(58) Field of Classification Search
CPC .......... A61B 90/50; A61B 17/02; A61B 34/30
See application file for complete search history.

(56) References Cited

U.S. PATENT DOCUMENTS 6,129,319 A   10/2000  Metelski
8,462,358 B2   6/2013  Becker et al.
(Continued)

FOREIGN PATENT DOCUMENTS

CN    203622451 U   6/2014
DE    19526915 A1   2/1997
(Continued)

*Primary Examiner* — Amy J. Sterling
(74) *Attorney, Agent, or Firm* — BakerHostetler

(57) ABSTRACT

A holding apparatus, in particular a holding arm and/or tripod, for medical purposes, comprises a proximal end for attaching the holding apparatus to a base and a distal end for receiving an add-on device; at least one first and one second arm segment, where the first arm segment is connected to a first joint and the second arm segment is connected to a second joint, where each joint is releasable and lockable; an operating device for releasing and/or locking the respective joint for putting the holding apparatus into a desired pose; and a first display unit which is arranged on the first joint and a second display unit which is arranged on the second joint. The first and/or second display unit is configured to display at least one status of the holding apparatus and/or of an add-on device that is different from the releasing and/or locking of the respective joint. The invention further relates to a method.

25 Claims, 11 Drawing Sheets

(51) Int. Cl.

| | |
|---|---|
| *B25J 1/02* | (2006.01) |
| *B25J 1/12* | (2006.01) |
| *B25J 9/06* | (2006.01) |
| *B25J 11/00* | (2006.01) |
| *B25J 13/02* | (2006.01) |
| *B25J 13/08* | (2006.01) |
| *B25J 19/06* | (2006.01) |
| *A61B 34/30* | (2016.01) |
| *A61B 17/02* | (2006.01) |
| *F16M 13/02* | (2006.01) |
| *A61B 90/57* | (2016.01) |
| *A61B 17/00* | (2006.01) |
| *A61B 90/00* | (2016.01) |
| *A61B 90/96* | (2016.01) |
| *B25J 18/04* | (2006.01) |

(52) U.S. Cl.
CPC . *B25J 1/12* (2013.01); *B25J 9/06* (2013.01); *B25J 11/0005* (2013.01); *B25J 11/005* (2013.01); *B25J 13/02* (2013.01); *B25J 13/082* (2013.01); *B25J 13/084* (2013.01); *B25J 13/085* (2013.01); *B25J 19/06* (2013.01); *F16M 13/022* (2013.01); *A61B 90/96* (2016.02); *A61B 2017/00115* (2013.01); *A61B 2090/0807* (2016.02); *A61B 2090/508* (2016.02); *A61B 2090/571* (2016.02); *B25J 18/04* (2013.01); *F16M 2200/021* (2013.01)

(56) References Cited

U.S. PATENT DOCUMENTS

| | | | |
|---|---|---|---|
| 9,274,014 | B2 | 3/2016 | Janik et al. |
| 10,528,840 | B2* | 1/2020 | Bailey ................ G06K 9/00208 |
| 2003/0167061 | A1 | 9/2003 | Schlegel et al. |
| 2005/0209614 | A1 | 9/2005 | Fenter et al. |
| 2013/0221183 | A1 | 8/2013 | Volkenand et al. |
| 2018/0049737 | A1* | 2/2018 | Swayze ................ A61B 17/064 |
| 2018/0215050 | A1 | 8/2018 | Kassow |

FOREIGN PATENT DOCUMENTS

| | | |
|---|---|---|
| DE | 102009009549 A1 | 9/2010 |
| DE | 102011004371 A1 | 8/2012 |
| DE | 102014016823 A1 | 5/2016 |
| EP | 1728482 A1 | 12/2006 |
| EP | 1958587 A1 | 8/2008 |
| EP | 2455053 A1 | 5/2012 |
| EP | 2873403 A1 | 5/2015 |
| EP | 2965874 A2 | 1/2016 |
| JP | 201162792 A | 3/2011 |
| JP | 2012218139 A | 11/2012 |
| JP | 2013006239 A | 1/2013 |
| JP | 3183355 U | 5/2013 |
| JP | 2013180124 A | 9/2013 |
| JP | 20148071 A | 1/2014 |
| WO | 2007005555 A2 | 1/2007 |
| WO | 2016075241 A1 | 5/2016 |

* cited by examiner

MEDICAL HOLDING ARM HAVING ANNULAR LED DISPLAY MEANS

CROSS-REFERENCE TO RELATED APPLICATIONS

This application is a continuation of U.S. patent application Ser. No. 15/751,846, filed Feb. 9, 2018, and published as U.S. Patent App. Pub. No. 2018/0235724 on Aug. 23, 2018, which is a National Stage of International Patent App No. PCT/EP2016/069167, filed Aug. 11, 2016, which claims priority to European Patent Application No. EP 15180826.8-1659, filed Aug. 12, 2015, the disclosures of which are incorporated by reference in their entirety.

FIELD OF THE INVENTION

The invention relates to a holding apparatus, in particular a holding arm and/or tripod, for medical purposes, in particular for holding surgical mechatronic assistance systems and/or surgical instruments. The invention also relates to a method.

BACKGROUND

Holding arms included among the holding apparatuses of the kind initially specified have long been known from the prior art and are specifically used in surgery to relieve an operator of static holding work. Such a holding arm is used to hold a mechatronic assistance system and/or a surgical instrument, such as a manipulator, an endoscope, a surgical clamp or the like. The holding arms initially specified have proved their usefulness for holding endoscopes, in particular. In endoscopic surgery, an operator generally operates an instrument with both hands, while an assistant holds the endoscope in order to make the operating area visible on a screen. Holding the endoscope over a protracted period is very tiring. The aforementioned holding arms are increasingly used for that reason.

One such holding arm is known from DE 195 26 915 B4, for example. The holding apparatus for medical purposes disclosed therein has a connection member and a holder for surgical tools, as well as an arm arranged between the holder and the connection member. The arm is connected to the holder and to the connection member, or to an adjacent arm via a joint, and can be overcoupled to a pneumatically operable device for selectively locking and releasing the joints, wherein the device locks the joints by the action of a mechanical spring which exerts a braking force on the joint, and wherein the device can be pneumatically switched to a joint-releasing mode against the force of that spring. An actuator by means of which a valve can be opened is disposed at the proximal end of the arm, so that the separate joints of the arm can be adjusted. When the actuator is released, the valve is closed again, thus locking the joints. One disadvantage with this holding arm is that all the joints are opened simultaneously, with the result that positioning can be difficult.

A similar holding arm is disclosed in EP 1 958 587 B1. The holding arm disclosed therein likewise has a plurality of joints, and a touch-sensitive sensor for actuating the joints is provided. The sensor is disposed on the holding arm adjacent to the medical instrument, so that the operator comes into contact with the touch-sensitive sensor on gripping the medical instrument, thus causing the joints of the holding arm to be released. The aforementioned problem of poor positioning arises here also.

Another problem encountered with both of the aforementioned holding arms is that it is not clear to the operator whether all the joints are in fact open, how wide open they are, and which movements are permitted.

A carrier system for carrying or supporting medical technology devices in a treatment room is also known from EP 2 455 053 B1. The carrier system has a tripod for mounting in the treatment room, at least one joint or at least one mechanism by which the tripod can be moved in the treatment room, an operating aid for operating at least one part of the carrier system in order to control a movement of the tripod, and a feedback system for generating a signal or feedback indicating operation of the correlating part of the carrier system by means of the operating aid. The carrier system is characterised in that the feedback system has at least one luminous element which identifies or characterises the part of the carrier system or the respective joint or the respective mechanism locally on the tripod at the respective position of the mechanism or at the respective joint, typically by illumination. In the embodiment shown, the carrier system has two arms which are pivotable about pivot axes arranged parallel to each other. A short, cylindrical piece is provided at each joint, and an oval-shaped lamp is arranged in that cylindrical piece. The operating unit is provided in the form of a remote control unit and has buttons for releasing each joint. The respective lamp on the respective joint lights up when the button is pressed, the aim being to make it easier, especially in dark operating theatres, to press the right button and thus to release the right joint and to receive feedback about it.

The disadvantage here is that a lamp lights up only when the respective button on the remote control is pressed, i.e. when the joint is actuated.

SUMMARY OF THE INVENTION

The object of the present invention is therefore to improve the safety with which such a holding apparatus is operated, and to improve its user-friendliness.

The invention solves the object, in a holding apparatus of the kind initially specified, having a proximal end for attaching the holding apparatus to a base and a distal end for receiving an add-on device, at least one first and one second arm segment, wherein the first arm segment is connected to a first joint and the second arm segment is connected to a second joint, wherein each joint is releasable and lockable, an operating device for releasing and/or locking the respective joint for putting the holding apparatus into a desired pose; and a first display unit which is arranged on the first joint and a second display unit which is arranged on the second joint, wherein the first and/or second display unit is configured to display at least one status of the holding apparatus and/or of an add-on device that is different from the releasing and/or locking of the respective joint. The status is preferably displayed by displaying a representation of it. The invention is based on the realisation that there may be circumstances in which displaying only the release and/or locking of a respective joint, i.e. its actuation, is not sufficient to provide adequate safety and/or user-friendliness. The at least one status of the holding apparatus and/or of an add-on device that is different from the releasing and/or locking of the respective joint can be displayed additionally or alternatively to displaying the release or locked status of the holding apparatus. The display thus provides the operator with other indications that go beyond the pure status of releasing and/or locking of a joint, and with which the user-friendliness and/or safety is then enhanced. The display unit may be electrical, mechanical or electronic and may operate using visual and/or acoustic indicators.

According to a first preferred embodiment, the display units each have at least one light source. In such an embodiment, representation of the status takes the form of the light source(s) lighting up. This is a particularly simple way of embodying the display units. Furthermore, this visually perceptible display unit is also perceptible when visibility is poor. The light source is preferably configured to shine in two or more different colours, so it is possible for a different colour to be assigned to different statuses, thus improving safety and user-friendliness even more.

In one preferred development, the display units have at least one display for displaying the status. At least one of the display units preferably has such a display. It is particularly preferred that each of the display units has a display for displaying the status. Such a display may take the form of a touch-sensitive display, for example, and preferably displays not only in graphical, but also in alphanumeric form. It is thus conceivable and preferred that patient data, for example, such as age, weight, diseases and the like, are displayed, as well as data from an operation, such as data on physiological function data or anaesthesia data. In such a case, it is also conceivable that the display units are not used exclusively to display the status of the holding apparatus, but also to display a status of a patient and/or an environment, or to display information.

According to another preferred embodiment, at least one display unit is substantially designed as a ring around a pivot axis of the respective joint. The display unit is designed, for example, as an annular light source, for example as a ring of LED elements, as an annular OLED, as an annular display or the like. An LED ring may be designed, for example, with one, two or more rows of LEDs. The substantially annular display unit is preferably coaxial with the pivot axis of the respective joint. As a result, the display unit is visible from every side of the pivot axis and is simultaneously an indicator for the orientation of the pivot axis. At least two such display units are preferably arranged at a joint, namely in such a way that they are both arranged coaxially with the pivot axis.

According to a preferred development of the invention, the status is an operational readiness status of the holding apparatus. The display unit is configured, for example, to shine in a first colour when the holding apparatus is ready for operation, and to shine in a second colour when it is not ready for operation. This is preferably indicated by all the display devices shining and/or flashing simultaneously. It is thus conceivable and preferred that, after switching on the holding apparatus, an internal microprocessor initially checks the operational readiness, and depending on the result the operational readiness status is displayed by means of the display units. This enables an operator to recognise immediately whether the holding apparatus is ready for operation and can be used, for example, in a surgical operation, or whether there is a defect or the like.

In another preferred embodiment, the status is a distance between an add-on device and an edge of a predefined operating area of the holding apparatus. An orientation of the holding apparatus can be detected by orientation sensors in the joints, or the like, thus making it possible to determine a distance between an add-on device which is received at the holding apparatus, or a section of the holding apparatus itself, and an edge of a predefined operating area. It is particularly preferred that the display devices indicate the distance visually. It is preferred, for example, that the display devices change their luminous intensity, for example by increasing it, or change from a first to a second colour, and/or emit a warning sound, in order to indicate the distance. The display devices may shine discretely in two colours, for example, and the proportion of the one colour is reduced when the holding apparatus is moved towards the edge.

It is preferred that the status also signifies a distance between a current pose of the holding apparatus and a predefined pose of the holding apparatus. This helps a surgeon to move the holding arm into the correct pose. Some or all of the display devices can be configured, for example, to shine orange when the pose has not yet been reached, and to change progressively to a green colour when the respective joint has reached the respective predefined pose. This significantly improves not only the safety, but also the user-friendliness of the holding apparatus, and a surgeon receives feedback immediately and directly about whether the holding apparatus is in the correct pose.

It is also possible here, or in another variant, for the display units to be configured to display a direction in which at least one joint is to be moved in order to move the holding apparatus from the current pose into the predefined pose. This is preferably done by flashing, rotating a pattern, varying the brightness, or varying the colour. Some or all of the joints are preferably locked automatically when the predefined pose is reached. Such a predefined pose can be obtained via an OP system, for example, or from preoperative planning software.

In another preferred embodiment, the status is an operational status of a controller for the holding apparatus. The holding apparatus preferably has a controller, for example a microcontroller or the like. In one operational status, a controller performs the following tasks, for example: storing the current pose; calculating a pose; retrieving previously stored poses; writing surgical records; recording/processing data captured by means of the add-on device; uploading software to microcontrollers in joints; displaying a progress bar when working and/or when processing data, and the like. The user thus receives immediate feedback about the current status of the holding apparatus, for example whether the currently adopted pose is stored, or the like. The operator can also recognise whether data which have been recorded or processed by means of the add-on device are being stored and/or processed.

According to another embodiment, the status is a communication status of the holding apparatus with the add-on device. This means that the display units indicate whether and preferably how the holding apparatus communicates with the add-on device, i.e. with which intensity, data volume, or the like. If, for example, data are transmitted from the add-on device to the holding apparatus, in particular to an interface provided for that purpose at the distal end, this is indicated by means of the display device. This can be done, for example, by illuminating at least one display device in a predefined colour.

It is further preferred that the status is a movement of the holding apparatus. Accordingly, the display device preferably indicates when a joint is moved. According to this embodiment, for example, a joint is initially released by means of an operating device, but the display unit does not indicate this release, or not only this release, but rather the actual motion of the joint. To achieve that purpose, the holding arm preferably has orientation sensors in at least one and preferably in all the joints.

When the status is a movement, this also includes, in one preferred embodiment, that the display devices indicate when the holding apparatus as a whole is moved, in particular without changing its pose. This is then the case, for example, when the holding apparatus is attached by means of its proximal end to an operating table, and the latter is moved, that is to say linearly displaced, pivoted, rotated, or the like. In such a case, the motion of the holding arm is indicated by at least one display unit, for example by it lighting up, flashing, changing colour, emitting an acoustic signal, or the like. A change in the position of the operating table may mean a change in position of objects arranged on it, or also in the position of the patient, with the result that a relative orientation of the holding apparatus to the patient may change, which in turn may cause dangers to arise. Safety is therefore significantly improved with this embodiment also.

It is preferable that the status of motion also includes any movement of a joint that is in the locked state. If the holding apparatus is heavily loaded, individual brakes in the joints may "slip", and a joint may move even though it is locked. According to this embodiment, any such movement is detected by an orientation sensor, in particular, and the respective display units indicate such movement. This is preferably done by the display unit lighting up, changing the intensity with which it shines, changing its colour, flashing, changing the frequency with which it flashes, or by it emitting a warning sound, or the like.

In another preferred configuration, the first display unit and the second display unit are configured to emit infrared radiation. By emitting infrared radiation, the holding apparatus can be detected by a conventional surgical navigation system which has infrared sensors for detecting OP equipment. OP equipment which can be incorporated into the infrastructure of a conventional surgical navigation system, of the kind that can be purchased from the firm of Brainlab in Germany, uses infrared flashes to detect equipment within the navigation area. Due to the display units being configured to emit not only light in the visible wavelength range, but also light in the infrared wavelength range, it is possible for the holding apparatus to be detected by the navigation system. When such a display unit which emits infrared light is provided at each joint, it is possible for the surgical navigation system to detect and process the pose of the holding apparatus.

It is further preferred that the display units have infrared LEDs. The display units preferably have LEDs which emit light in the visible wavelength range. The LEDs for visible light and the infrared LEDs are arranged alternatingly, for example, and are coupled in pairs, so that the pattern which is displayed in the visible wavelength range and the pattern which is displayed in the infrared wavelength range are identical. By the same token, however, it is also preferred that different patterns be displayed.

The display units are preferably configured to display the status of the holding apparatus and/or of an add-on device by means of the infrared radiation. This allows the status to be communicated to the surgical navigation system. The surgical navigation system is preferably configured to detect the different signals that are broadcast as infrared radiation from the holding apparatus, and to process those signals accordingly.

It is particularly preferred that the display units are configured to emit infrared light when the holding apparatus moves. As described in the foregoing, a preferred embodiment is one which displays the motion of the holding apparatus by means of the display units. Preferably, this is likewise done using infrared radiation. It may be sufficient, for example, if light is emitted by a single LED when the holding apparatus moves at the respective joint, or by means of a single infrared LED when the entire holding apparatus moves at all its joints. In this way, it is possible to inform the surgical navigation system that a movement of the holding apparatus is taking place.

It is preferable that the display units which can emit infrared light are also used to indicate all other statuses of the holding apparatus, as described in the foregoing. This can be carried out in substantially the same manner as in the visible wavelength range.

In another preferred embodiment, the holding apparatus has a measuring device for measuring at least one physical and/or chemical value, and the status is the measured value. The holding apparatus has a force sensor, for example, and a force is applied at the add-on device and/or at the distal end of the holding apparatus, for example due to contact between the holding apparatus and a patient, and the status is the measured force. The status could equally well be the pH value, for example. The display device preferably indicates whether the measured value lies within predetermined threshold values. A two-colour code, for example red and green, may be used for this purpose. When the display unit indicates red, then this is an indicator, according to one embodiment, that a measured value, for example a measured force, lies beyond the predetermined thresholds. In such a case, the surgeon should adjust the pose of the holding apparatus to one in which the force is within the predetermined range.

At the distal end of the holding apparatus, and more specifically at the interface, a plurality of force sensors are preferably arranged to form a measuring device for measuring at least one physical value. The plurality of force sensors are preferably arranged in such a way that it is also possible to measure torque resistance at the distal end of the holding apparatus, in particular at an interface. As an alternative, an individual force/torque sensor may also be provided there. This is particularly advantageous when a retractor, for example, or a similar instrument which is meant to act on the patient or on some other object with a predetermined force or with a force within a predetermined range is received at the distal end. By moving the holding apparatus, the operator can set the force exactly, and the latter is displayed by means of the display units, and the operator can move the holding apparatus in such a way that the joints are locked whenever the force has reached approximately the predetermined value. It is thus possible, for example, to pull on one part of a tissue with a predetermined force. It is preferable that the holding apparatus simultaneously comprises a timekeeper unit which measures the duration that said force or a similar force is applied. It may be advantageous, for example, to apply a specific force to specific areas of tissue in the patient for a specific period of time only, and subsequently to change the amount of force applied and the direction in which the force is applied. This, too, can be indicated to an operator by means of the display units. It is advantageous, for example, when the duration is also indicated, in addition to the force. Injuries to the patient can be prevented in this way. Persons assisting during an operation are also relieved of strain and do not have to exert a static holding force (i.e. a specific amount of force applied in a specific direction) for a protracted period. The holding apparatus may additionally be designed such that, when a surgeon moves the holding apparatus in such a way that the force increases, one or more joints are locked by an internal control unit when a maximum force is reached. This prevents too great a force being exerted on the patient. It is simultaneously preferred that automatic locking of the joints is indicated by means of the display units so that the surgeon receives feedback in that regard. This helps to prevent any traumatisation.

According to another embodiment, the display devices are configured to indicate whether a respective joint is released or locked. The holding apparatus has operating device for releasing and/or locking the respective joint. According to this embodiment, the display devices indicate additionally whether a respective joint has been released or locked by means of the operating device.

In a second aspect of the invention, the initially specified object of a holding apparatus of the kind initially specified is achieved by a holding apparatus comprising: a proximal end for attaching the holding apparatus to a base and a distal end for receiving an add-on device; at least one first and one second arm segment, wherein the first arm segment is connected to a first joint and the second arm segment is connected to a second joint, wherein each joint is releasable and lockable; an operating device for releasing and/or locking the respective joint for putting the holding apparatus into a desired pose, wherein the operating device is configured to release the respective joint when there is contact between an operator and one of the first and second arm segments, and a first display unit which is arranged at the first joint, and a second display which is arranged at the second joint, which are configured to indicate whether a respective joint is released or locked. According to the invention, the holding apparatus according to this aspect comprises an operating device which is designed to release the associated joint upon contact between an operator and one of the first and second arm segments.

According to this embodiment, therefore, the operating device is adapted to release the first joint when contact occurs between an operator and the first arm segment and to release the second joint when contact occurs between an operator and the second arm segment, which means that whenever there is contact between an operator and a respective arm segment, only the associated joint is released, according to this embodiment. This release is then indicated by means of the display units. This makes it possible to move individual joints intuitively and thus to adjust the holding apparatus segment by segment and to bring it into a desired pose. By this means, positioning can be carried out with greater precision, because each segment can be adjusted separately and incrementally. It is likewise possible to contact a plurality of segments substantially simultaneously, so that several joints are simultaneously released, and that this releasing is simultaneously indicated, and that the joints are adjustable. It is possible in this way to bring the holding apparatus into a desired pose in a simple manner, and in particular intuitively, with the display units indicating that individual joints have been released, thus providing the operator with immediate and intuitive feedback.

In addition to the first and second arm segments, further arm segments which are each associated in like manner with a respective joint are preferably provided. The arm segments themselves are substantially rigid and preferably rod-shaped. The expression "rod-shaped" here includes not only substantially straight arm segments, but also slightly or strongly curved arm segments. In such a holding apparatus, the arm segments and joints always alternate, and the holding apparatus may end with a joint or with a segment or with a connection member at the distal and at the proximal end. The holding apparatus can be attached to a base with its proximal end. Alternatively, the base may be coupled securely to the holding apparatus, or the holding apparatus can be removed from the base. In one embodiment, the base is in the form of an operating table, and the holding apparatus can be coupled to an operating table. The holding apparatus can preferably be coupled to a standard rail provided on the operating table. Such standard rails are generally provided on operating tables, so a standard interface can be provided on the holding apparatus to couple it to the standard rail of an operating table. Normal operating tables are also assembled from separate segments. For coupling purposes, the segments have matching, generally manufacturer-specific coupling points on their front sides. The holding apparatus can preferably be attached to the operating table via such a coupling point. A manufacturer-specific adapter may be provided for that purpose at the proximal end. Alternatively, the base is provided as a separate apparatus, for example a stand which can be set up on the floor of an operating theatre. In another alternative, the base is configured as a holder which can be attached to a wall or ceiling of an operating theatre, for example.

The holding apparatus is preferably configured as a "passive" holding apparatus, and for that reason has joints which are only actively braked, but not driven joints as is often the case with robotic holding apparatuses. Each joint is therefore releasable and lockable only, but cannot be driven. As a result, the holding apparatus is simple in design and does not need a complex controller in order to operate it.

According to a first preferred embodiment of the invention, the operating device has contacting elements which are adapted so that an operator comes into contact with them, wherein a first contacting element of the operating device is arranged on the first arm segment and a second contacting element is arranged on the second arm segment. When contact is made with the first contacting element, the first joint is preferably released, and when contact is made with the second contacting element, the second joint is preferably released. The contacting elements are used to detect contact between the user and the arm segment. The contacting elements are preferably arranged on a surface of the respective arm segment. The contacting elements may extend over the entire arm segment or may occupy only a section of it. Each contacting element preferably extends around approximately half the circumference about a central axis of an arm segment. As a result, the contacting elements can be easily reached in every pose of the holding apparatus, and an operator can easily come into contact with it.

According to another preferred embodiment, each contact portion has two, three or more contact elements arranged substantially opposite one another or equally distributed on the arm segment, as the case may be. According to this embodiment, it is preferred that the associated joint is released only when there is contact with both or with two of the three or more, or with all the contact elements. The contact portion preferably consists of the two, three or more contact elements, so there is contact with the contact portion only when at least two contact elements are contacted by the operator. By arranging the two contact elements substantially opposite each other, preferably in relation to a plane containing a central axis of the arm segment, it is possible to distinguish between inadvertent contact, for example by an arm of an operator, and intentional contact, namely deliberate gripping of the arm segment, so according to this embodiment the joint is released only when the arm segment is gripped, in particular by the operator's hand, in which case the two opposite sides of the arm segment are contacted. In order to operate the holding arm and to bring the holding apparatus into a desired pose by means of the operating device, the arm segment must therefore be gripped by the operator in such a way that he comes into contact with the two or three contact elements of the contact portion, whereupon the associated joint is released by the operating device and the arm segment can be moved.

According to a preferred development of the invention, the contact elements are provided in the form of pushbuttons. Pushbuttons are particularly simple elements which can not only be detected visually by the operator, but also provide direct tactile feedback when the button is pressed. Such a pushbutton may be provided in the form of a simple closing contact of an electrical circuit, for example, or as a capacitive switch. As long as both the pushbuttons according to this embodiment are pressed, the joint associated with the respective arm segment is released; as soon as the operator releases both or even just one of the two pushbuttons, the joint is locked again by the operating device.

According to one preferred alternative embodiment, the contact elements are provided in the form of touch-sensitive sensors. The sensors are preferably substantially planar in shape and extend over a substantial portion of the surface of the respective arm segment. The sensors are preferably provided in the form of pressure-sensitive sensors, capacitive sensors, heat-sensitive sensors and/or as optical sensors. Such sensors have the advantage that they can cover a larger area, which means the operator does not have to contact the arm segment quite as exactly, but that it is sufficient if the operator's grip is substantially around the arm segment and thus comes into contact with the sensor or sensors.

In another preferred embodiment, the operating device is designed to release the associated joint according to the intensity of contact. What is meant by intensity here is a pressure and/or force which is applied by the operator. It is possible in this way for the operator to control a degree of freedom with the force that he applies when gripping. It is thus conceivable and preferred that the associated joint is only partially released when the intensity of contact is low, so that the arm segment can be moved only slowly and against a resistance. Whenever the intensity is high and thus when the grip is strong, the joint is opened completely, so the arm segment can be moved with substantially no resistance. The joint can also be partially released by releasing it intermittently in different frequencies.

It is preferred that when there is contact between an operator and one or more arm segments, several or all joints, in particular those joints situated between two contacting arm segments, are released.

In another preferred embodiment of the holding apparatus according to the second aspect of the invention, the first and/or second display unit is configured such that at least one status of the holding apparatus and/or of an add-on device that is different from the releasing and/or locking of the respective joint is additionally displayed. With regard to this preferred development of the invention, reference is made to the entire description of the first aspect of the invention, provided above.

It should be understood that the first and the second aspect of the invention have identical and similar sub-aspects, as specified in the dependent claims, in particular. Reference is thus made to the entire description provided above regarding the preferred features and their effects.

In a third aspect of the invention, the object referred to at the outset is achieved by a method of the kind initially specified, for displaying for displaying at least one status of a holding apparatus and/or of an add-on device, in particular of a holding apparatus according to any one of the embodiments described in the foregoing, that is different from the releasing and/or locking of a joint, said method comprising the steps of: detecting the status; displaying the status, in particular by means of a display unit which is substantially designed as a ring around a pivot axis of the respective joint.

It should be understood that the third aspect of the invention and the first and/or second aspect of the invention have identical and similar aspects as specified in the dependent claims, in particular. Reference is made to the entire description above in that respect.

BRIEF DESCRIPTION OF THE DRAWINGS

The invention shall now be described in more detail with reference to one embodiment and with reference to the attached drawings, in which.

DETAILED DESCRIPTION

Figure 1:
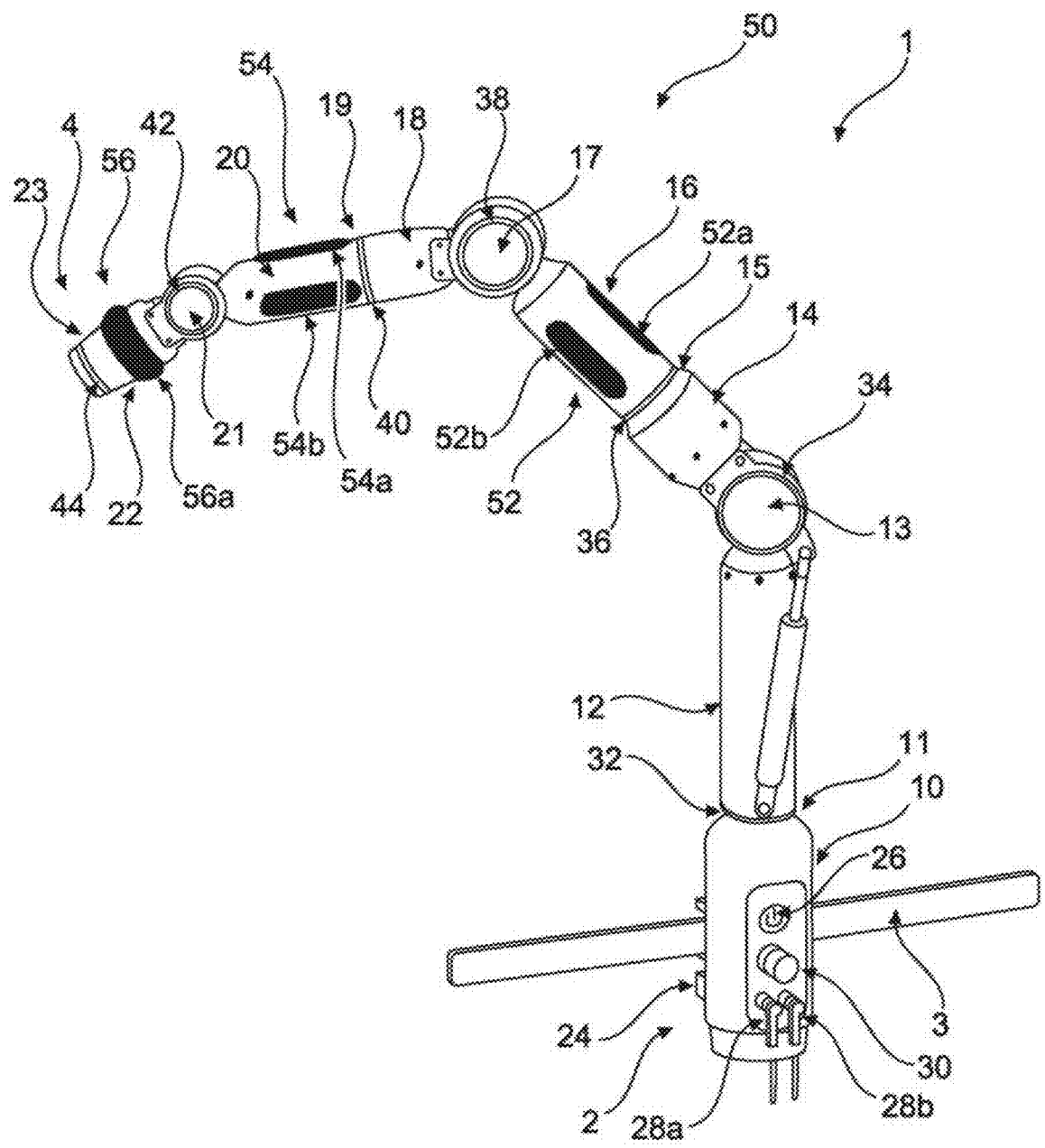
FIG. 1 shows a side view of a holding apparatus according to the invention.

FIG. 1 shows a holding apparatus 1 in the form of a holding arm. The holding apparatus has a proximal end 2 for attaching the holding apparatus 1 to a base 3. According to this embodiment, base 3 is designed as a standard rail of an operating table (the operating table is not shown in FIG. 1). Holding apparatus 1 also has a distal end 4 for receiving an add-on device 6 (cf. FIG. 2).

Figure 2:
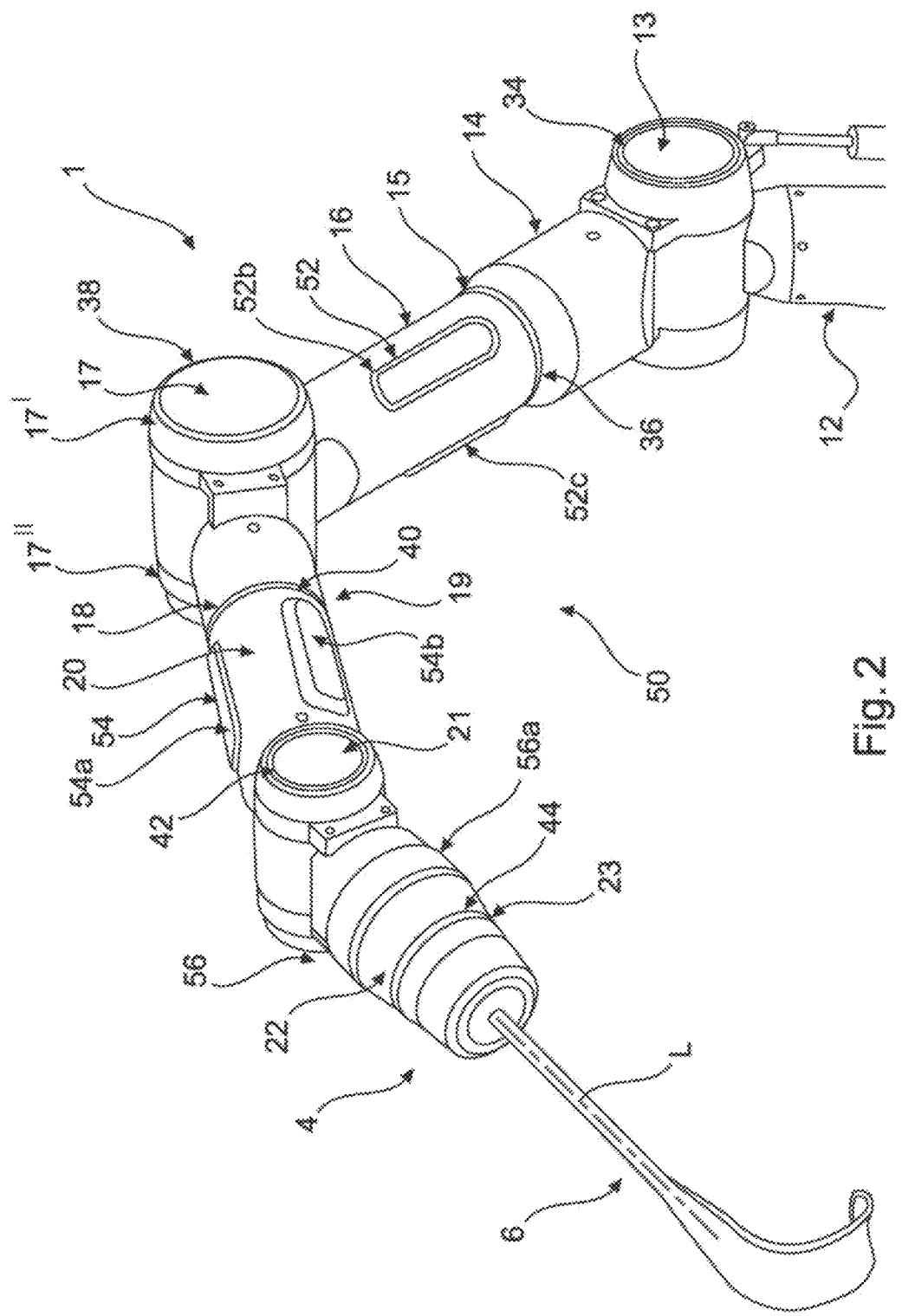
FIG. 2 shows a perspective view of the holding apparatus in FIG. 1, with an add-on device received at the distal end.

The holding apparatus shown in FIGS. 1 and 2 has seven arm segments 10, 12, 14, 16, 18, 20, 22, with joints 11, 13, 15, 17, 19, 21, 23 provided between the individual arm segments 10-22. The first arm segment 10 forms the proximal end 2 and has clamping jaws 24 by means of which holding apparatus 1 can be secured to base 3. Also provided on arm segment 10 are a power button 26 for switching on the entire holding apparatus, two connections 28a, 28b via which the holding apparatus can be supplied with power and data, such as control signals and the like, and via which the data can be transferred from the holding apparatus to external units such as surgical systems, and an emergency stop button 30.

Joints 11, 15, 19 and 23 are designed as pivot joints, and joints 13, 17 and 21 as hinge joints. Referring to FIG. 1, this means that the rotational axes of joints 11, 15, 19 and 23 are substantially in the plane of the drawing, whereas the rotational axes of joints 13, 17 and 21 are substantially perpendicular to the plane of the drawing.

At each joint 11, 13, 15, 17, 19, 21, 23, holding apparatus 1 has a display unit 32, 34, 36, 38, 40, 42, 44 for displaying a status of the holding apparatus and/or of an add-on device (cf. FIG. 2).

According to this embodiment, display units 32, 34, 36, 38, 40, 42, 44 are designed substantially as annular light sources, in particular as LED rings. The central axis of each ring is substantially coaxial with the respective rotational axis of joint 11, 13, 15, 17, 19, 21, 23. Whereas a single LED ring is provided for each of joints 11, 15, 19, 23, two LED rings are provided for each of joints 13, 17 and 21. The two LED rings are provided at the front and rear joint portions 17', 17" (marked with reference signs in FIG. 2 by way of example only). This means that each display unit is observable at all times.

According to this embodiment (cf. FIGS. 1 and 2), the holding apparatus also has an operating device 50. Through the of operating device 50, the holding arm can be brought into a desired pose, operating device 50 being adapted to release the associated joint 11, 13, 15, 17, 19, 21, 23, upon contact between an operator and one of the seven arm segments 10, 12, 14, 16, 18, 20, 22. For that purpose, operating device 50 according to this embodiment has three contact areas 52, 54, 56, with each contact area 52, 54, 56 being arranged on a different arm segment 16, 20, 22. One contact area 52 is thus arranged on arm segment 16, one contact area 54 on arm segment 20 and one contact area 56 on arm segment 22. Each contact area 52, 54, 56 has separate contact elements 52a, 52b, 52c, 54a, 54b, 54c and 56a. The individual contact elements are designed as touch-sensitive surfaces, such that one or more associated joints are released on contact between an operator and a respective contact element.

According to this embodiment, three contact elements 52a, 52b, 52c, 54a, 54b, 54c are provided on each of arm segments 16 and 20, and on arm segment 22 an annular contact element 56 is arranged which can also be rotated about its central axis in order to control functions at an interface of an add-on device received at the distal end 4.

In this embodiment, contact elements are associated with the individual joints 11, 13, 15, 17, 19, 21, 23 according to the following rules. Upon contact between an operator and arm segment 16, i.e. with contact elements 52a, 52b, 52c of contact area 52, joints 15, 13 and 11 are released. An operator can now control three degrees of freedom; this is an extent of control which can be well managed manually, and in which the holding apparatus can be brought into a desired pose manually. When an operator comes into contact with arm segment 16, and joints 15, 13 and 11 are released, it is preferred that the corresponding display units 32, 34, 36 indicate such release, i.e., in the embodiment shown in FIGS. 1 and 2, by the LED ring lighting up.

Joints 19 and 17 are released upon contact with arm segment 20, i.e. with contact area 54 and in particular with contacting elements 54a, 54b, 54c. It is preferable, accordingly, that this is displayed by display units 36, 38. Finally, when there is contact with arm segment 22, i.e. with contact area 56 and in particular with contact element 56a, joints 21 and 23 are released, which is preferably indicated by means of display units 42, 44.

Referring now to FIG. 2, an add-on device 6 in the form of a retractor is received at distal end 4. One or more force sensors, by means of which a tensile force acting in the direction of longitudinal axis L can be detected, are arranged at the interface at distal end 4 at which retractor 6 is received. By means of these sensors, it is also possible to detect the respective torques at the interface about longitudinal axis L and also perpendicularly thereto. Display unit 44 is configured to indicate this status of add-on device 6, and in particular to indicate whether a particular force is within predetermined limits. During surgical operations, there is a risk that too great a force is applied to a retractor 6 for a protracted period, with adverse effects on the tissue which is being held away from the operating area. This problem can be mitigated or prevented by measuring said force and determining whether it is within predetermined limits.

Figure 3A:
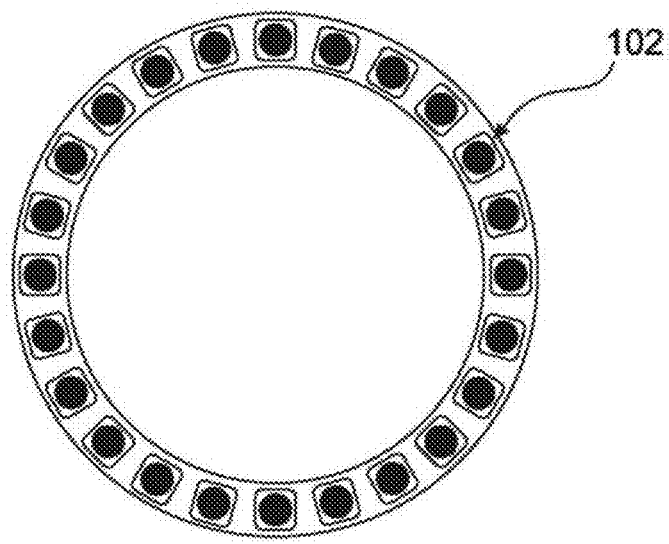
FIGS. 3a, 3b show two schematic views of a display unit.

FIGS. 3a-7c show different embodiments of display units according to the invention, as well as their use to indicate a status of the holding apparatus and/or of an add-on device that is different from the releasing and/or locking of the respective joint. All the display units shown in FIGS. 3a-7c are designed as single rows. FIG. 3a shows a display unit 100 in a preferred embodiment of the invention. Display unit 100 is ring-shaped and has a plurality of annularly arranged LEDs 102 (in FIG. 3a, only one is marked with a reference sign). According to the embodiment shown in FIGS. 3a, 3b, LEDs 102 are oriented within the plane of the drawing in such a way that the display unit according to this embodiment can be used, for example, as a display unit 34, 38 or 42. Whereas display unit 100 is shown in a first state in FIG. 3a, the same display unit 100 is shown in a second state in FIG. 3b. It should be understood that the two states can be an OFF state in FIG. 3a and an ON state in FIG. 3b. It is also conceivable, alternatively, that FIG. 3a shows display unit 100 shining in a first colour, whereas in FIG. 3b it shines in a second, different, colour. Such visualisation is used, in particular, to indicate the released and/or locked state of the holding apparatus, i.e. to indicate whether a respective joint is locked or released. Different variants of the invention are conceivable and preferred in this regard. In a first embodiment, the display unit 100 shown in FIGS. 3a, 3b is connected to an internal controller of the holding apparatus 1 (cf. FIGS. 1, 2). It is preferred in this regard that display device 100 shines in a first colour when touch contact between the operator and one of the contact elements 52a, 52b, 52c, 54a, 54b, 54c, 56a is detected. It is preferred in this regard that the respective joint is not released immediately upon contact, but after a delay of two seconds, for example. What is displayed by the display unit, therefore, is not the releasing or locking of the joint, but the fact that the operating device has been actuated, so an operator still has enough time to discontinue or to confirm his action before the joint is actually released. It is also possible to arrange for only one display unit 100 to light up when all the joints are released. In another preferred embodiment, an additional display unit which is not assigned to a specific joint is provided in arm segment 10 (see FIG. 1). This display unit indicates that all the joints in the holding apparatus are released. In such a case, it is conceivable that the individual display units 32, 34, 36, 38, 40, 42, 44 associated with the respective joints do not indicate separately that the joints are released.

In another preferred variant of the embodiment (FIGS. 3a, 3b), display units 100 are coupled to a signal line of the brakes in the joints. In such an embodiment, a display unit 100 lights up whenever a voltage is applied to the brake in order to open it. Alternatively or additionally thereto, display unit 100 is coupled to a bus system for the brakes, such that the display units pick up the control signal for the brake and light up due to said control signal, thus indicating that the brake has received a control signal for its release.

Figure 3B:
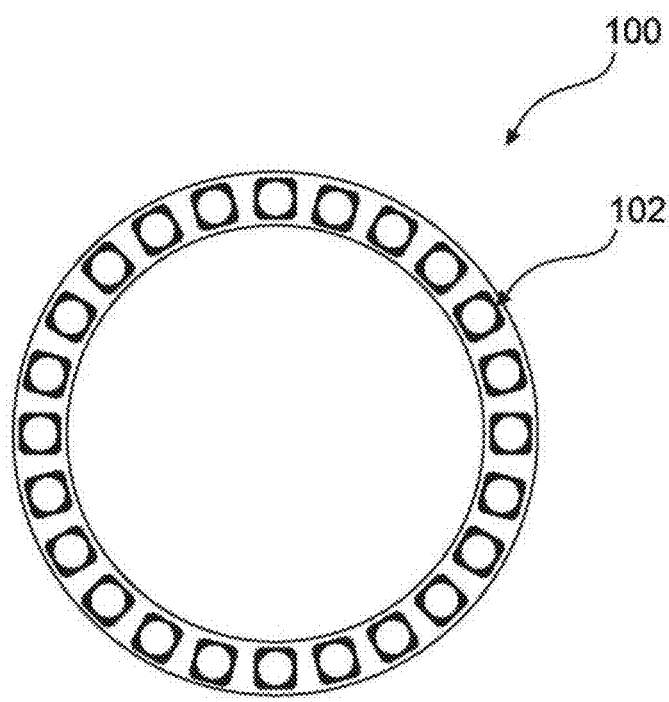

The embodiment shown in FIGS. 3a, 3b, in which a display unit 100 switches between two or more different colours (and in particular switches in its entirety, meaning that all the LEDs 102 have the same colour), is also preferably used to indicate a status of the holding apparatus or of the add-on device that is different from the releasing or locking of the respective joint. It is also preferred that, depending on the specific application in which the holding apparatus is used, the display units 100 shine in a colour provided for such use. If, for example, the holding apparatus is used in a ENT operation, all the display units shine green (preferably when the brakes are locked). When the same holding apparatus is used in abdominal surgery, all the display units shine blue (preferably when the brakes are locked). A surgeon is thus able to see immediately whether the holding apparatus is set correctly for the present application, and/or is correctly supplied with data from a surgical system. This may be advantageous when different applications require different behaviour by the brakes in the joints, for example, or when different amounts of force may be exerted on the holding apparatus, or when only a specific number and group of add-on devices are permitted. The respective data in this regard are provided and/or polled via interfaces, preferably at a distal and a proximal end of holding apparatus 1, and are processed in an internal controller which then sends a respective signal to display units 100.

In another variant, the display unit 100 shown in FIGS. 3a, 3b is coupled to one or more position sensors in the joints, preferably with the respective display unit being coupled to a position sensor in the respective joint. In such an embodiment, the status different from locking and/or releasing is the status of the movement of a joint. This means that an operator can initially release one or more joints by means of operating unit 50, which is not indicated then by the display unit (N). The respective display unit does not light up until the operator moves a joint. It is thus conceivable that the operator grips arm segment 20 (cf. FIG. 1) and in doing so comes into contact with contact area 54. Joint 19 and also joints 17 and 15 are released thereby. If the operator then pivots joint 17 only, then only display unit 38 lights up. In this way, an operator receives feedback about which joint is being moved here, and can thus check what he is doing.

Figures 4A, 4B, 4C:
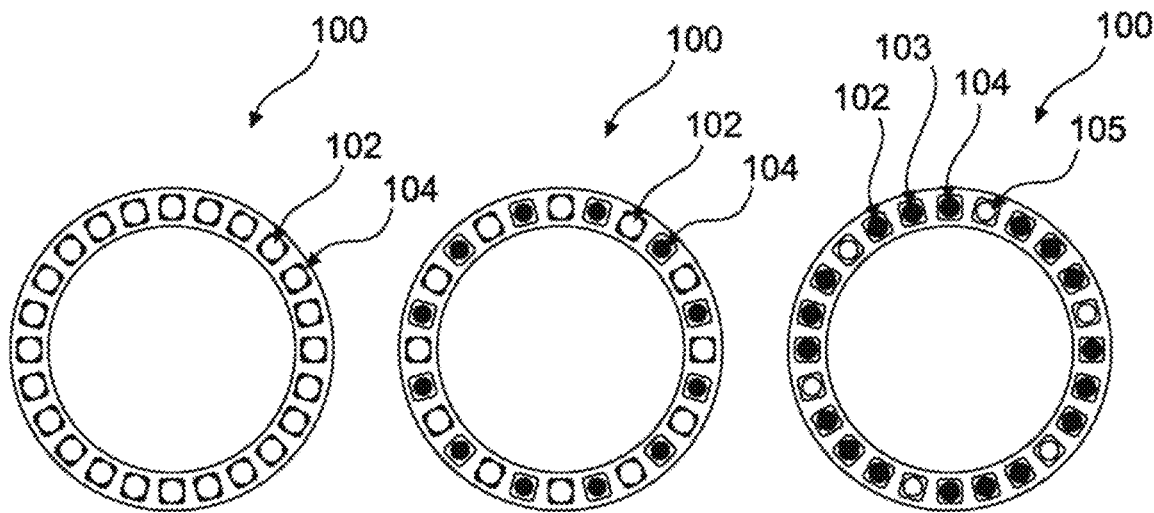
FIGS. 4a-4c show three schematic views of a display unit.
Figures 5A, 5B, 5C:
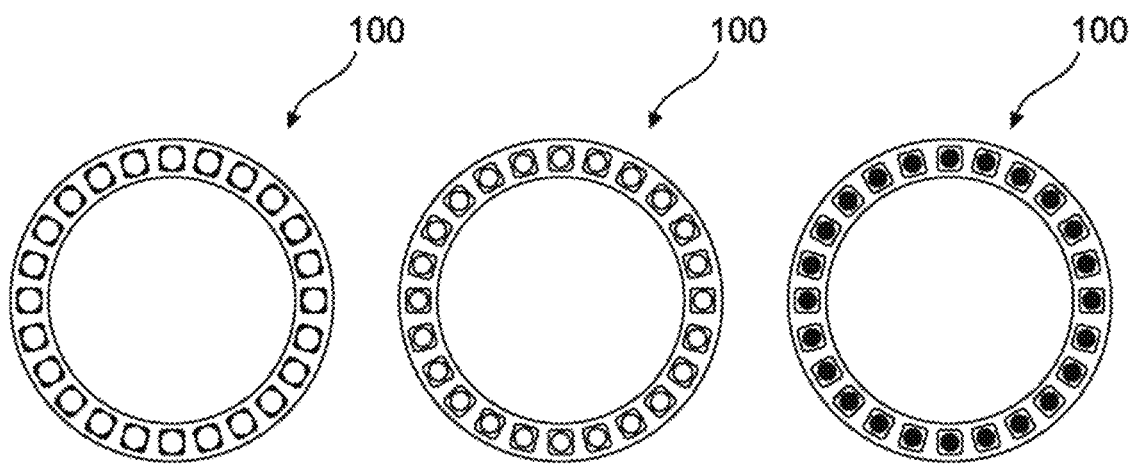
FIGS. 5a-5c show three schematic views of a display unit.

FIGS. 4a-4c and 5a-5c show a display unit 100 of the kind that is basically known from FIGS. 3a, 3b, in a second embodiment. FIGS. 4a-5c show display units which can not only switch between two or more different colours, but in which individual LEDs 102, 103, 104, 106 can take different colours (cf. FIGS. 4a-4c), or in which the luminous intensity is changed (cf. FIGS. 5a-5c). This is particularly advantageous when the holding apparatus is being positioned, and the operator is to be given feedback about such positioning. In one variant, it is preferred that a display unit 100, of the kind shown in FIGS. 5a-5c, lights up when a joint is moved, for example that display unit 38 lights up when joint 17 is moved. The luminous intensity can then be varied according to the speed of movement. In one such case, FIG. 5a shows a display unit 100 which indicates that there is no movement, FIG. 5b illustrates a movement performed at a medium speed, and FIG. 5c shows a movement performed at a high speed.

Position sensors in the joints of holding apparatus 1 are also used, preferably, for measuring, in particular for measuring a movement. By operating holding apparatus 1 and moving holding apparatus 1, it is thus possible, for example, to measure a distance between two points, for example between portions of a patient's tissue. When the holding apparatus designed in this manner is put into a respective measuring mode, it is preferred that the display units indicate this. This is shown by way of example in FIGS. 4a-4c.

Figures 6A, 6B, 6C:
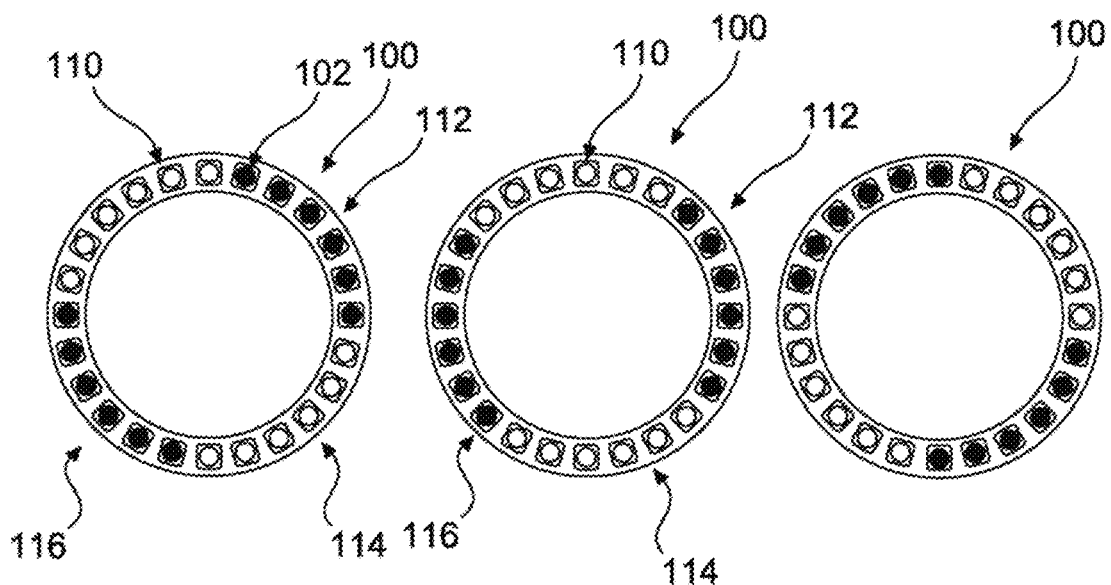
FIGS. 6a-6c show three schematic views of a display unit.

FIGS. 4a-4c also illustrate a function in which an operator moves the holding apparatus from a current pose to a desired pose, and in such a case the status indicated is the distance to the desired pose. Whereas in FIG. 4a all the LEDs 102, 104 shine in one colour, thus indicating that the current pose is not identical to the desired pose, FIG. 4b shows display unit 100 indicating that the operator has moved the holding arm towards the desired pose; every second LED 102, 104 has a different colour, i.e. half of the LEDs shine in a first colour and the other half shine in a second colour. FIG. 4c illustrates that the operator has then moved the holding apparatus even further towards the desired pose; only every fourth LED 106 now has the first colour, whereas LEDs 102, 103, 104 have already adopted the second colour. When the desired pose has been reached, all the LEDs 102, 103, 104, 106 have then switched to the second colour, and the operator sees that he has reached the desired pose. It is preferable that all the brakes in the joints are automatically closed when the desired pose is reached, hence, that all joints are locked. FIGS. 6a-6c illustrate another way in which the display unit can indicate a measuring function or a measuring mode. Display unit 100, in the form of an LED ring, has four different sections 110, 112, 114, 116, having two different, alternating colours. The individual LEDs 102 (only one of which is marked with a reference sign in FIGS. 6a-6c) are then controlled by an internal controller in such a way that the pattern formed by the four sections 110, 112, 114, 116 rotates to the right in FIGS. 6a-6c, so that the individual sections 110, 112, 114, 116 "roam" with the movement of the respective arm segment. For example, if joint 17 is released and the section of the holding apparatus between joint 17 and the distal end 4 is pivoted, the individual sections 110, 112, 114, 116 move in the direction of the pivoting movement, at the respective speed, in order to indicate the status of the movement and to help the operator to see how quickly and by what angle he is pivoting that particular section of the holding apparatus.

Figures 7A, 7B, 7C:
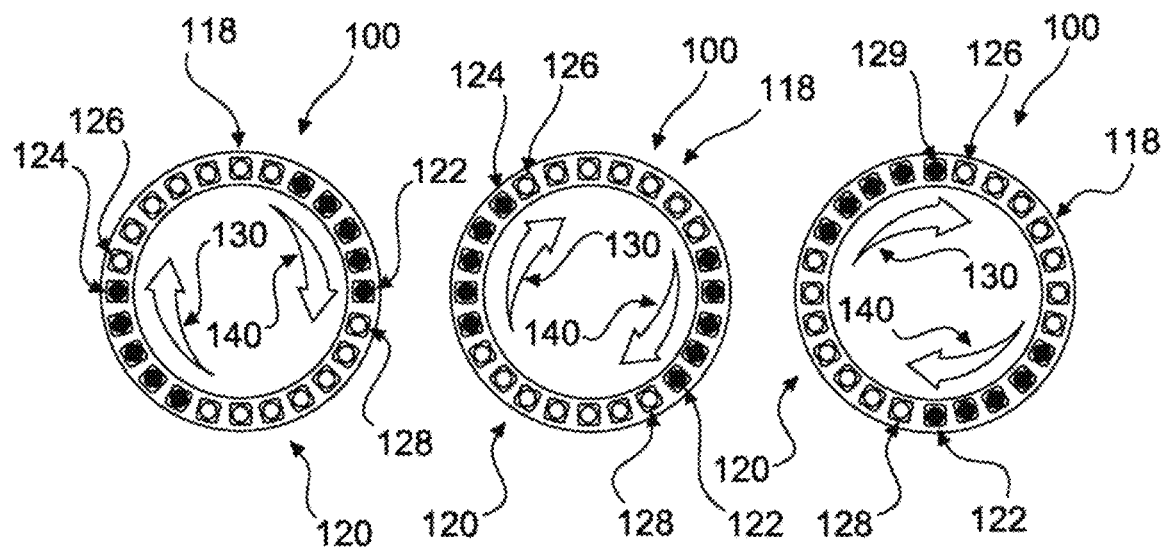
FIGS. 7a-7c show three schematic views of a display unit.

A similar illustration is shown in FIGS. 7a-7c, in which display device 100, designed as an LED ring, has two sections 118, 120. Each of these sections has a colour gradient, from an LED 122, 124 which shines in a first colour, to an LED 126, 128 which shines in a second colour. Arrows 130, 140 show the direction in which a pattern rotates.

Other embodiments of visualisation by means of a display unit 100 (as shown in FIGS. 3a, 3b, in particular) are ones where display unit 100 shines in a first colour as long as the arm does not pivot, or pivots within a defined and stored tolerance zone. The first colour is displayed until such time as the arm no longer pivots. This is preferred when ultrafine manipulators are received as add-on devices on the holding apparatus. In this way, an operator is notified to wait until the holding apparatus is within an acceptable tolerance zone. When the holding apparatus is pivoting, then any add-on device should not be moved any further. By means of the position sensors in the joints, it is also possible to detect when the holding apparatus is jolted, or when a joint is pivoted in its locked state against the force of the brake. This can be detected by means of position and/or orientation sensors and can be indicated by means of the display units. An operator thus receives feedback about whether the holding apparatus is still in the desired pose, or whether one joint has been moved against the force of the brake, for example.

A display unit of the kind shown in FIGS. 6a-7c is preferably also used to transfer a teaching, i.e. a sequence of poses (trajectory), to the holding apparatus. It may be advantageous, prior to an operation or the like, to go through different poses with the holding apparatus and to store and/or test those poses. In this regard, it is possible and preferred to put the holding apparatus in a teach mode, in which the poses gone through are detected and stored by the internal controller. The display units indicate this state accordingly, in particular with a pattern of the kind shown in FIGS. 7a-7c.

FIGS. 8a-9b illustrate a display unit 200 according to another embodiment, in the form of a double ring of LEDs. Display unit 200 (cf. FIG. 8a) has a first LED ring 202 and a second LED ring 204. A plurality of LEDs 206, 208 (only one of each marked with a reference sign) are arranged in each LED ring 202, 204. In such an embodiment, it is possible to control the two LED rings 202, 204 independently of each other. It should be understood that not every LED ring 202, 204 must be composed exclusively of one row of LEDs, but that each may have more than one row, with the rows then being preferably controlled in unison. It should also be understood that embodiments having three or more LED rings are preferred.

Figure 8A:
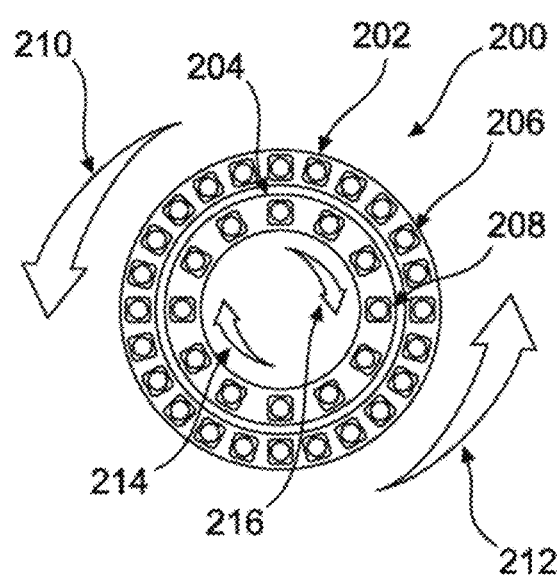
FIGS. 8a, 8b show another embodiment of a display unit.
Figure 8B:
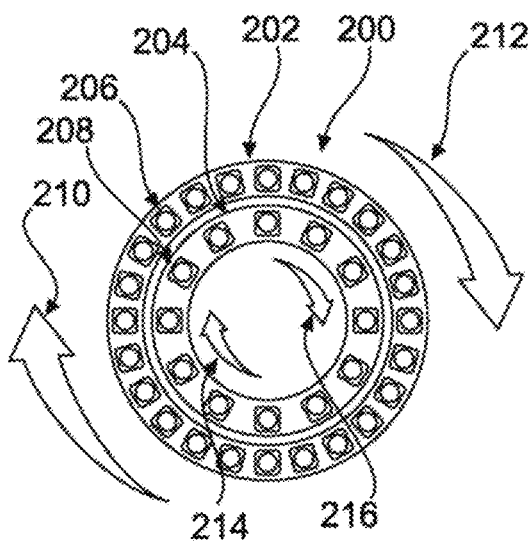

FIGS. 8a, 8b, for example, show that a rotating pattern is displayed on LED ring 202, 204, as described with reference to FIGS. 6a-7c, for example. In FIGS. 8a, 8b, arrows 210, 212 show a direction of rotation on the outer LED ring 202, whereas arrows 214, 216 illustrate the direction of rotation of the pattern on the inner LED ring 204. FIG. 8a shows that the pattern moves in opposite directions (arrows 210, 212 and 214, 216 point in opposite directions), FIG. 8b illustrates rotation in the same direction. Such a display (FIG. 8a) is preferred, for example, when two joints are released and these are moved in opposite directions, or are to move in such a way in order to reach a target pose. A display with rotation in the same direction (FIG. 8b) can be used to indicate that movement in the same direction is required.

Figure 9A:
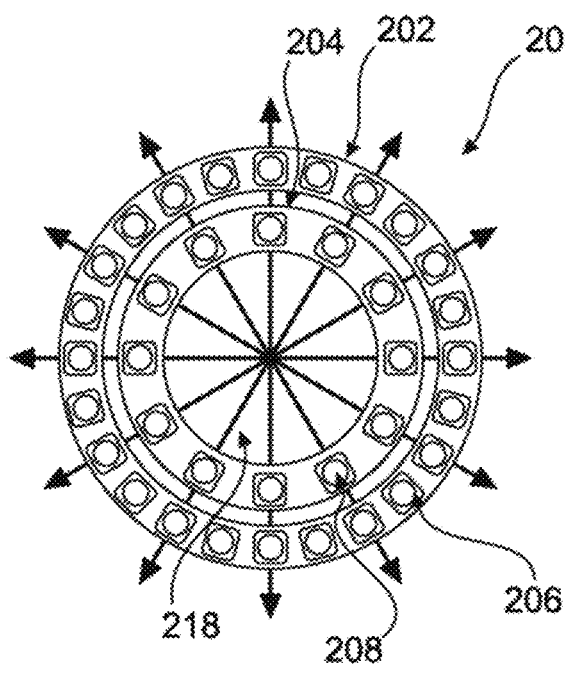
FIGS. 9a, 9b show another embodiment of a display unit.
Figure 9B:
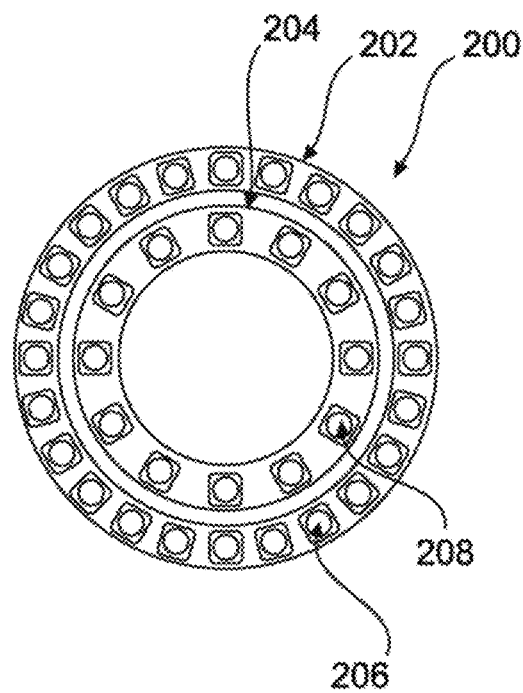

FIGS. 9a, 9b illustrates a pattern moving radially from the inside to the outside, as indicated by arrows 218. Such an effect is reinforced when three or more LED rings are provided. Visualisation with a pattern which runs from the outside to the inside, i.e. in the opposite direction to arrows 218, is conceivably preferred. Such visualisation is preferably used, in particular, to indicate an update of software modules by one or more joints, or by a central control unit.

Figure 10:
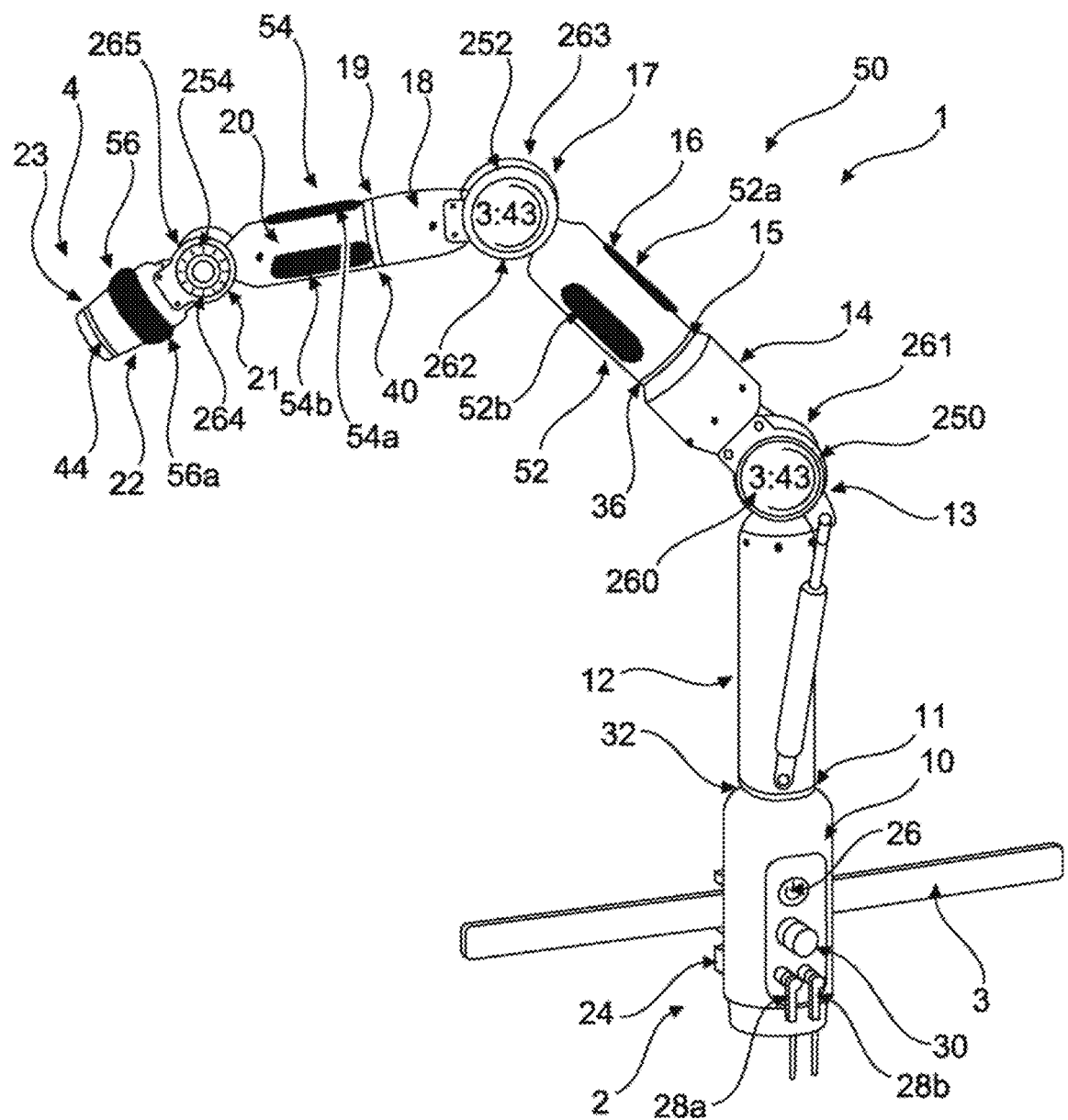
FIG. 10 shows another embodiment of a holding apparatus.

FIG. 10 illustrates another embodiment of holding apparatus 1. This is identical in many features to holding apparatus 1 as shown in FIGS. 1 and 2, so identical and similar elements are marked with the same reference signs in FIGS. 1 and 2. Reference is made in this respect to the entire description of FIGS. 1 and 2 in the foregoing. In the following, the principal focus is on the differences between the embodiments in FIGS. 1 and 2, and in FIGS. 10, 11 and 12, respectively.

Holding arm 1 has substantially the same structure as the holding arm shown in FIGS. 1 and 2, but with the difference that display units 250, 252, 254 each having two displays 260, 261, 262, 263, 264, 265 are arranged at the three articulated joints 13, 17, 21. Only displays 260, 262, 264 can be seen in FIG. 10; displays 261, 263, 265 are arranged on the rear side of holding apparatus 1 in FIG. 10, parallel to displays 260, 262, 264.

Displays 260, 261, 262, 263, 264, 265 are round in shape and are arranged with their central axis coaxial with the pivot axis of respective joint 213, 217, 221.

FIG. 10 shows displays 260, 262 displaying the period of time that the respective joint 13, 17 has already been in that position. This is particularly helpful when a specific sequence of movements is planned. In FIG. 10, display 264 shows an angular range in which arm segment 22 is inclined. By this means, an operator receives feedback about the orientation of the last arm segment on which the add-on device is received.

Figure 11:
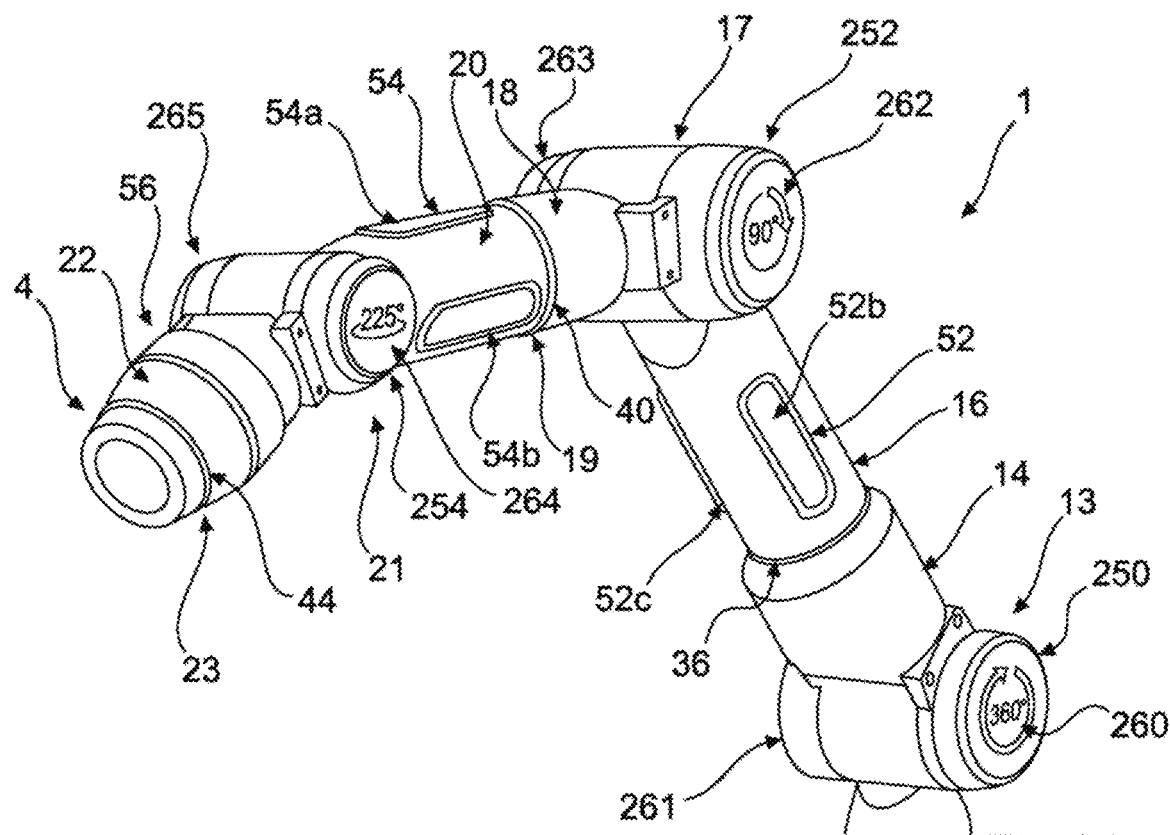
FIG. 11 shows another view of the holding apparatus shown in FIG. 10.
Figure 12:
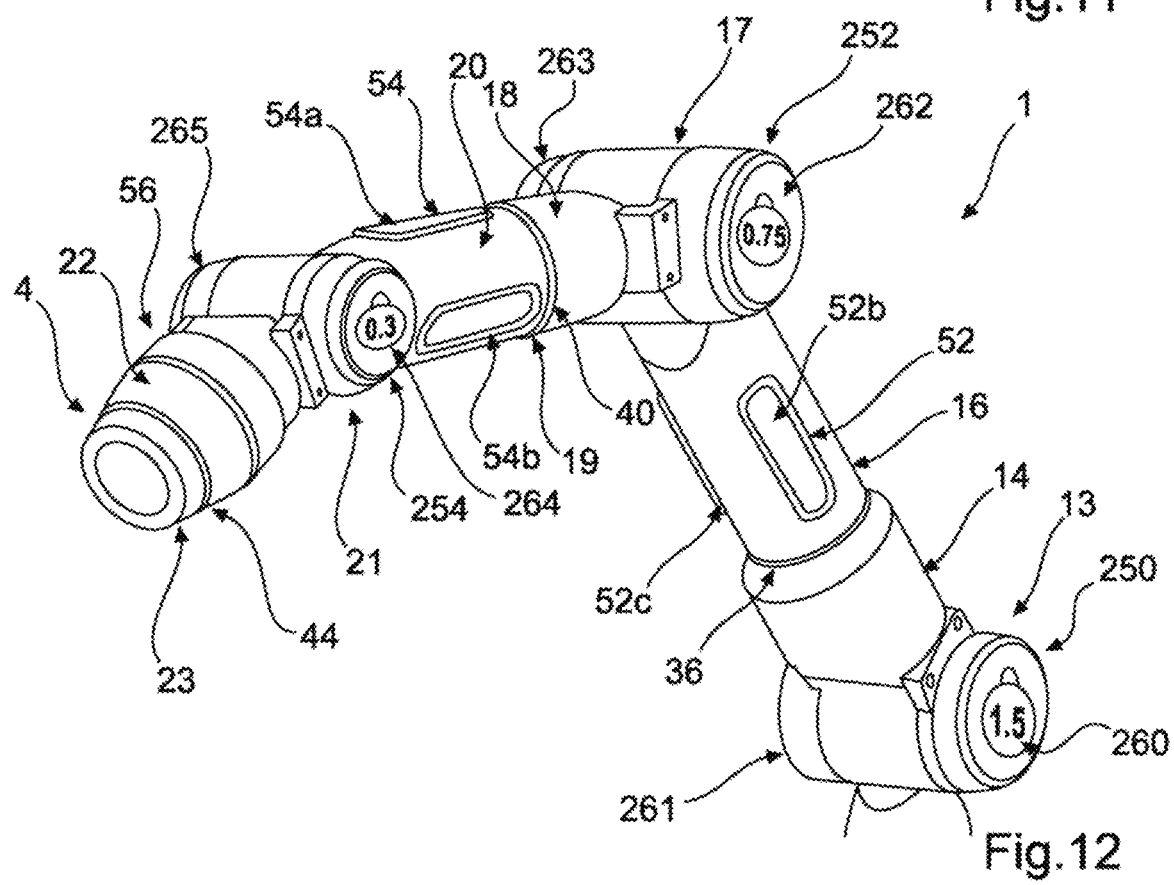
FIG. 12 shows another view of the holding apparatus shown in FIG. 10.

FIGS. 11 and 12 illustrate embodiments contrasting with other embodiments in which displays 260, 262, 264 are used to indicate a status that is different from releasing and/or locking.

According to FIG. 11, displays 260, 262, 264 indicate in which direction and by how many degrees a respective joint 13, 17, 21 may be pivoted before leaving an operating area of holding apparatus 1. Display 264 indicates not only the direction of rotation of joint 21, but also that of joint 19, which is indicated by the horizontal arrow on display 264. Such visualisation is also possible on displays 262, 260, but is not shown in this embodiment.

FIG. 12 shows another visualisation of a status of holding apparatus 1. The weight acting on the individual joints 13, 17, 21 is entered on displays 260, 262, 264, so an operator is able to estimate whether the load borne by holding apparatus 1 is still within an acceptable range, and also whether the load acting on an add-on device may be excessive.

When displays 260, 261, 262, 263, 264, 265 are used as display units, other indications of a status or the like are conceivable. The individual displays are preferably provided in the form of touch-sensitive displays and are also used for inputting profiles to holding apparatus 1. It is preferred, for example, that an on/off switch is displayed on display 260, 261, and that the holding apparatus can be switched on and off by touching display 260, 261. It is equally conceivable that a current pose of holding apparatus 1 is stored by touching a display 260, 261, 262, 263, 264, 265. Other displayed items include data transfer, patient data, patient images such as X-ray images, CT/MR images, planning steps, access to robotic control of an add-on device, as well as inputting commands for the add-on device, displaying a working environment, for example connections to other systems and the like.

Figure 13:
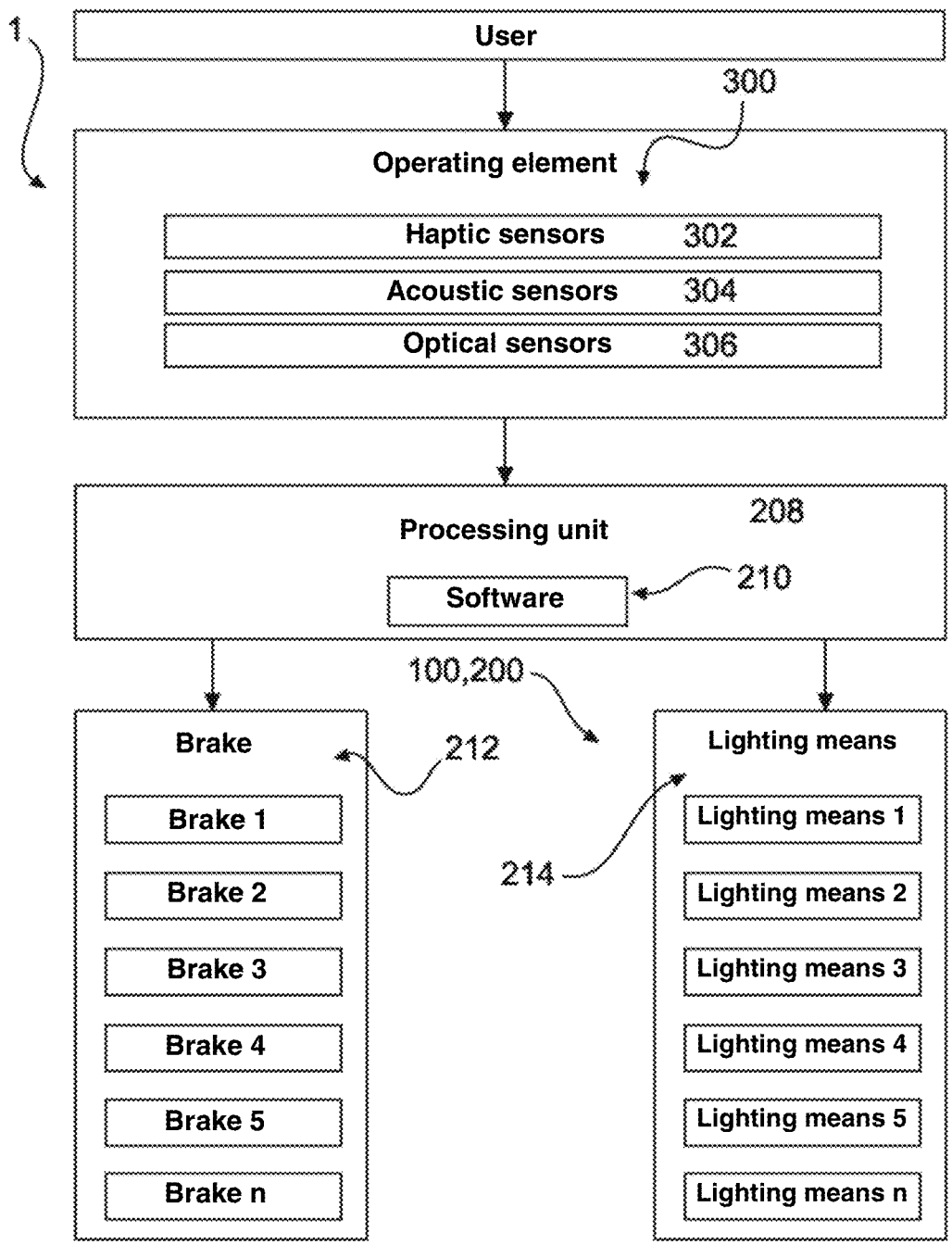
FIG. 13 shows a schematic diagram for a method, showing the structure of the holding apparatus according to the invention.
Figure 14:
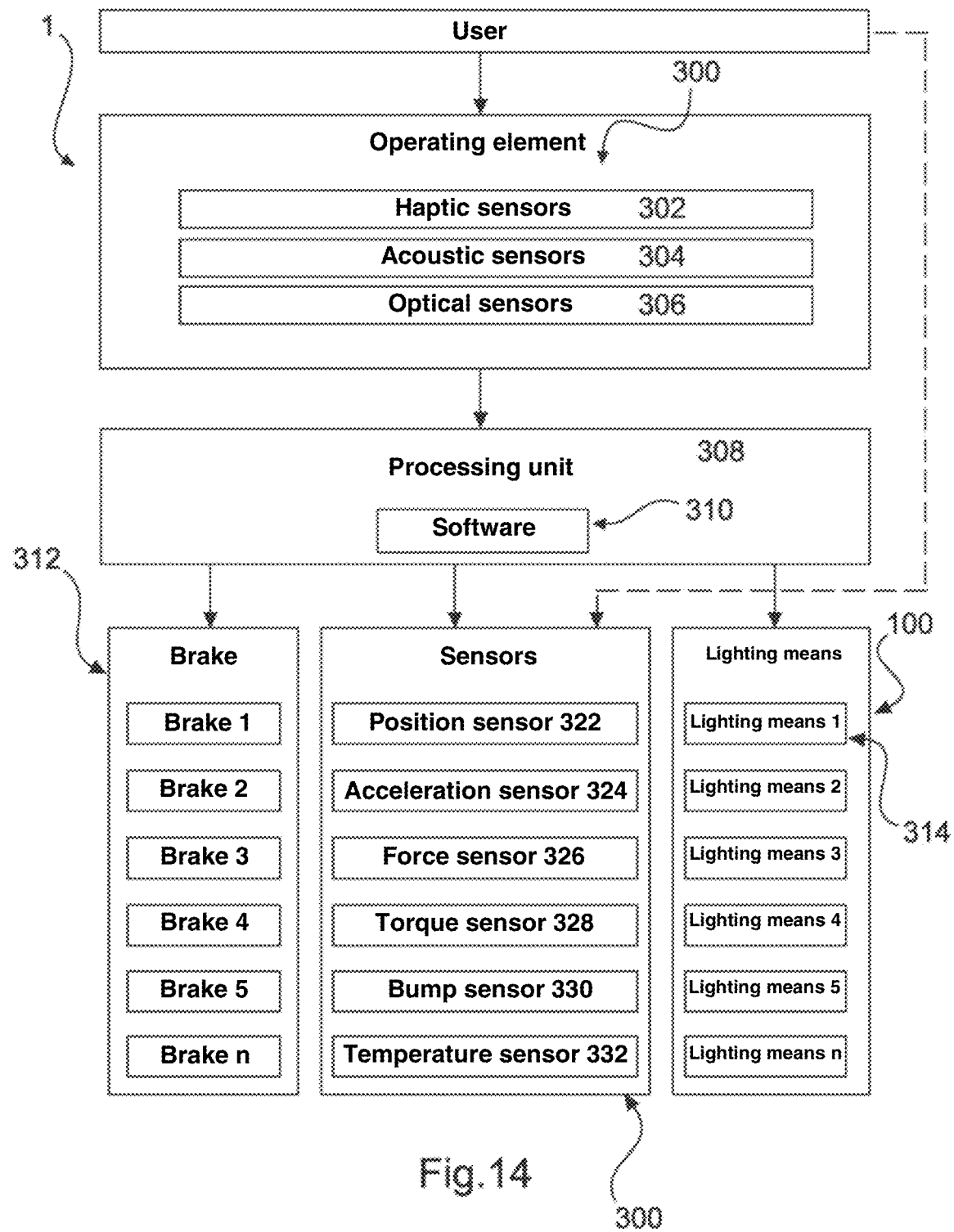
FIG. 14 shows a schematic diagram for a method, showing the structure of the holding apparatus according to the invention.

FIGS. 13 and 14 illustrate a basic structure of a system comprising a holding apparatus 1 and a user. Holding apparatus 1 comprises operating elements 300, which may include haptic sensors 302, acoustic sensors 304 and optical sensors 306. An example of a haptic sensor is operating device 50, as described in the foregoing. Internally, holding apparatus 1 has a processing unit 308 having a software module 310. Brakes 312, which are closed in an idle state and are opened by applying a voltage, are arranged in the joints. The holding apparatus is thus designed as a "passive" holding apparatus, in which all the joints are locked in the de-energised state. According to this embodiment, the display units are provided in the form of lighting unit 314, each of which is assigned to a joint and a brake. For example, lighting unit 1 is assigned to brake 1, lighting unit 2 to brake 2, etc. The individual lighting units are preferably provided in the form shown in FIGS. 1-7c. The processing unit is coupled to the operating elements and analyses the operating elements, in particular the haptic, acoustic or optical signals that are detected. These signals are analysed using software module 310, and the respective brakes 312 are released and/or locked. Release and/or locking is then indicated by the respective lighting unit 314. According to this embodiment, holding apparatus 1 is merely capable of indicating the release and locking of individual joints, but not any status other than that.

FIG. 14 shows how the display units are designed to display a status that is different from releasing and/or locking. Holding arm 1, which is basically similar in structure to the one shown in FIG. 13, has additional sensors 320. Sensors 320 include, for example, one or more position sensors 322, preferably in each joint, one or more acceleration sensors 324, preferably in each joint, one or more force sensors 326, preferably at the distal end 4, at least, of holding apparatus 1, one or more torque sensors 328, preferably in each joint and at the distal 4 and at the proximal end 2 of holding apparatus 1, at least one bump sensor 330 and at least one temperature sensor 332. Based on the data captured by sensors 320, the software 310 is configured to determine a status and to cause display units 100 to indicate said status, in particular by means of lighting unit 314.

Figure 15:
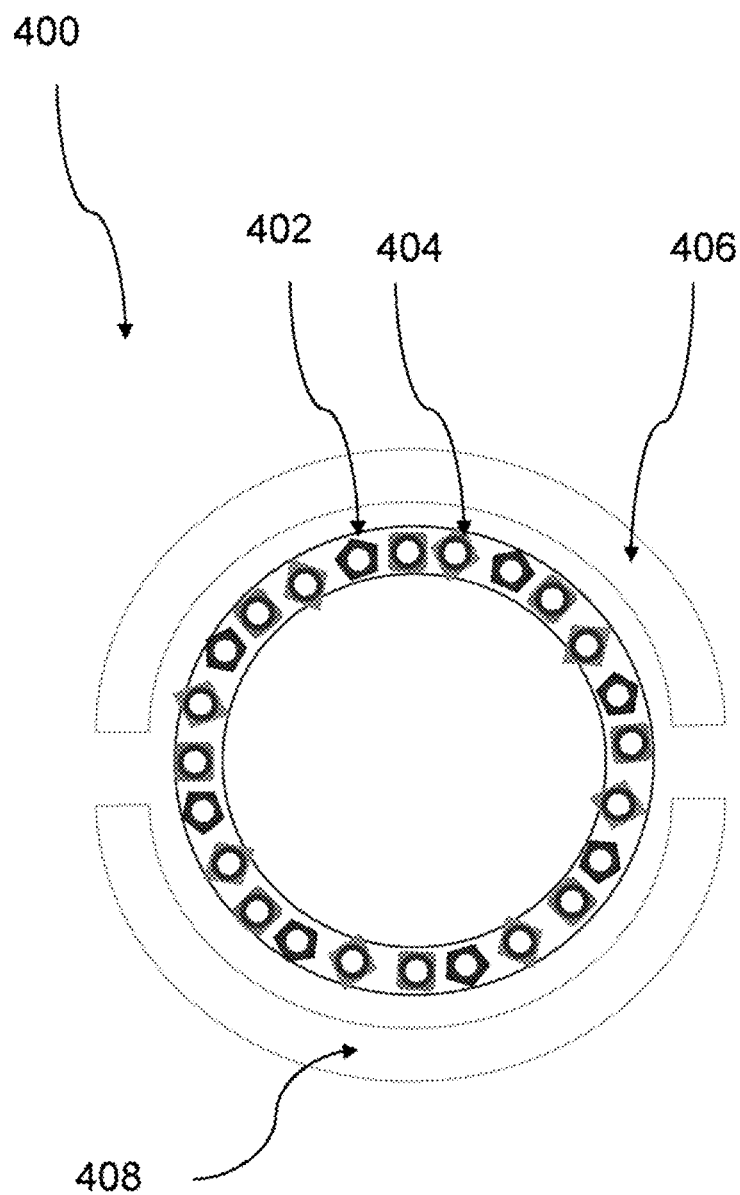
FIG. 15 shows a schematic view of a display unit which is configured to emit infrared radiation.

FIG. 15 illustrates another embodiment of a display unit 400. Display unit 400 is basically designed in accordance with the above embodiments, particularly with regard to its geometrical arrangement and functions. Unlike the first embodiments, the display unit 400 disclosed in this embodiment (FIG. 15) has not only LEDs 402 which emit light in the visible wavelength range (only one of which is marked with a reference sign in FIG. 15; cf. all the LEDs framed by a pentagon), but also infrared LEDs 404 which emit light in the infrared wavelength range (only one of which is marked with a reference sign in FIG. 15; cf. all the LEDs framed by a rhombus). This makes it possible not only to indicate the status of the holding apparatus in a visually perceptible form for humans, but also to indicate the status of holding apparatus by means of infrared radiation so that the status of the holding arm can be detected by a surgical navigation system which works with infrared sensors.

FIG. 15 also shows that two zones 406, 408 may be provided, i.e. that display unit 400, which is designed as a ring, may be divided as a whole into two parts. This allows two different statuses to be displayed by means of a single display unit 400, namely by providing the first zone 406 for a first status and the second zone 408 for a second status. Movement of the holding apparatus is indicated by zone 406, for example, whereas any opening of brakes in the joints is indicated by zone 408. All of the combinations described above are possible here and are hereby disclosed explicitly.

The invention claimed is:

1. A holding apparatus for holding a surgical mechatronic assistance system or a surgical instrument, the holding apparatus comprising:
 a proximal end for attaching the holding apparatus to a base and a distal end for receiving an add-on device;
 at least one first and one second arm segment, wherein the first arm segment is connected to a first joint and the second arm segment is connected to a second joint, wherein each joint is releasable and lockable;
 an operating device for releasing and locking the respective joint for putting the holding apparatus into a desired pose, the operating device being configured to release the respective joint upon contact between an operator and at least one of the first arm segment or the second arm segment; and
 a first display unit arranged on the first joint and a second display unit arranged on the second joint,
 wherein the first or the second display unit is configured to display at least one status of the holding apparatus or of the add-on device that is different from the releasing and locking of the respective joint.

2. The holding apparatus of claim 1, wherein the first and the second display units each have at least one light source.

3. The holding apparatus of claim 2, wherein the light source is configured to emit two or more different colors.

4. The holding apparatus of claim 1, wherein the first and the second display units have at least one display for displaying the status.

5. The holding apparatus of claim 1, wherein at least one of the first and the second display units is designed as a ring around a pivot axis of the respective joint.

6. The holding apparatus of claim 5, wherein the ring is a ring of LED elements.

7. The holding apparatus of claim 1, wherein the status is movement of the holding apparatus.

8. The holding apparatus of claim 1, further comprising orientation sensors arranged in at least one of the first joint and the second joint.

9. The holding apparatus of claim 1, wherein the first and the second display units are configured to display a direction in which at least one joint is to be moved in order to move the holding apparatus from a current pose into a predefined pose.

10. The holding apparatus of claim 9, wherein the direction is displayed by flashing, rotating a pattern, varying the brightness, or varying the color.

11. The holding apparatus of claim 9, wherein movement of the holding apparatus is displayed using a different color or a different pattern, from the one for the direction in which the at least one joint is to be moved in order to move the holding apparatus from the current pose into the predefined pose.

12. The holding apparatus of claim 11, wherein at least one of the first and the second display units is configured to display when the holding apparatus as a whole is moved without changing its pose.

13. The holding apparatus of claim 11, wherein at least one of the first and the second display units is configured to indicate movement of a joint in a locked state.

14. A holding apparatus for holding an add-on device, the holding apparatus comprising:
 a proximal end for attaching the holding apparatus to a base and a distal end for receiving the add-on device;
 at least one first and one second arm segment, wherein the first arm segment is connected to a first joint and the second arm segment is connected to a second joint, wherein each joint is releasable and lockable;
 an operating device for releasing and locking the respective joint for putting the holding apparatus into a desired pose, the operating device being configured to release the respective joint upon contact between an operator and at least one of the first arm segment or the second arm segment; and
 a first display unit arranged on the first joint and a second display unit arranged on the second joint,
 wherein the first or the second display unit is configured to display at least one status of the holding apparatus or of the add-on device, and
 wherein the first display unit and the second display unit are configured to emit infrared radiation communicating the at least one status of the holding apparatus or of the add-on device.

15. The holding apparatus of claim 14, wherein the first and the second display units comprise infrared LEDs.

16. The holding apparatus of claim 14, wherein the first and the second display units are configured to emit infrared light when the holding apparatus moves.

17. The holding apparatus of claim 14, wherein the first and the second display units each have at least one light source configured to emit two or more different colors.

18. The holding apparatus of claim 14, wherein at least one of the first and the second display units is designed as a ring around a pivot axis of the respective joint.

19. The holding apparatus of claim 14, wherein at least one of the first and the second display units is configured to display when the holding apparatus as a whole is moved without changing its pose.

20. The holding apparatus of claim 14, wherein at least one of the first and the second display units is configured to indicate movement of a joint in a locked state.

21. The holding apparatus of claim 1, further comprising a touch-sensitive sensor on at least one of the first arm segment or the second arm segment, the touch-sensitive sensor being configured to detect contact between the operator and at least one of the first arm segment or the second arm segment.

22. The holding apparatus of claim 21, wherein the touch-sensitive sensor is substantially planar and extends over a portion of the surface of the at least one of the first arm segment or the second arm segment.

23. The holding apparatus of claim 21, wherein the touch-sensitive sensor is a pressure-sensitive sensor, a capacitive sensor, a heat-sensitive sensor, or an optical sensor.

24. A system comprising:
a holding apparatus for holding an add-on device, the holding apparatus comprising:
a proximal end for attaching the holding apparatus to a base and a distal end for receiving the add-on device;
at least one first and one second arm segment, wherein the first arm segment is connected to a first joint and the second arm segment is connected to a second joint, wherein each joint is releasable and lockable;
an operating device for releasing and locking the respective joint for putting the holding apparatus into a desired pose, the operating device being configured to release the respective joint upon contact between an operator and at least one of the first arm segment or the second arm segment; and
a first display unit arranged on the first joint and a second display unit arranged on the second joint,
wherein the first display unit and the second display unit are configured to emit infrared radiation communicating at least one status of the holding apparatus or of the add-on device; and
a navigation system configured to detect and to process the infrared radiation communicating the at least one status of the holding apparatus or of the add-on device.

25. The system of claim 24, wherein the navigation system is configured to process the infrared radiation to determine the pose of the holding apparatus.

* * * * *